United States Patent
Alaofi et al.

(10) Patent No.: US 12,187,814 B1
(45) Date of Patent: Jan. 7, 2025

(54) STAPLED ANTIMICROBIAL PEPTIDE

(71) Applicant: KING SAUD UNIVERSITY, Riyadh (SA)

(72) Inventors: Ahmed Lafi Alaofi, Riyadh (SA); Mudassar Ahmad Shahid, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/581,115

(22) Filed: Feb. 19, 2024

(51) Int. Cl.
*C07K 7/02* (2006.01)
*A61K 38/00* (2006.01)
*A61P 31/04* (2006.01)
*A61P 35/00* (2006.01)

(52) U.S. Cl.
CPC ............... *C07K 7/02* (2013.01); *A61P 31/04* (2018.01); *A61P 35/00* (2018.01); *A61K 38/00* (2013.01)

(58) Field of Classification Search
None
See application file for complete search history.

(56) References Cited

PUBLICATIONS

Duplantier and van Hoek, Frontiers in Immunology, Jul. 2013, vol. 4, Article 143, 14 pages (Year: 2013).*
Dean et al., BMC Microbiology 2011, 11:114 (Year: 2011).*
Luong et al., J. Med. Chem. 2022, 65, 3026-3045 (Year: 2022).*
Nell et al., Peptides 27, 2006, 649-660 (Year: 2006).*
Su et al., Front. Chem. 10:840131, Apr. 2022 (Year: 2022).*
Mourtada et al., Nat Biotechnol. Oct. 2019; 37(10): 1186-1197 (Year: 2019).*
Su, Z. et al., Design, Synthesis, and Antitumor Activity Study of All-Hydrocarbon-Stapled B1-Leu Peptides, Front. Chem. 10: 2022.
Luong, H.X. et al., Application of the All-Hydrocarbon Stapling Technique in the Design of Membrane-Active Peptides, J. Med. Chem. 65(4): pp. 3026-3045 (2022).
Mohamed, M.F. et al., Targeting Methicillin-Resistant *Staphylococcus aureus* with Short Salt-Resistant Synthetic Peptides, Antimicrob. Agents Chemother. 58(7): pp. 4113-4122 (2014).
Phillips, et al., "Design and Structure of Stapled Peptides Binding to Estrogen Receptors", Journal of the American Chemical Society. vol. 133, pp. 9696-9699, 2011.

* cited by examiner

*Primary Examiner* — Melissa L Fisher
*Assistant Examiner* — Joseph Fischer
(74) *Attorney, Agent, or Firm* — Nath, Goldberg & Meyer; Joshua B. Goldberg

(57) ABSTRACT

A stapled antimicrobial peptide having the amino acid sequence FFRKSKEK-S5-GKE-S5-KRIV (SEQ ID NO: 1) and its use as an antimicrobial and anticancer agent are provided.

6 Claims, 1 Drawing Sheet

Specification includes a Sequence Listing.

STAPLED ANTIMICROBIAL PEPTIDE

SEQUENCE LISTING

The instant application contains a Sequence Listing which has been submitted in XML format via Patent Center and is hereby incorporated by reference in its entirety. Said XML copy, created on Oct. 3, 2023, is named 3309239U.xml and is 642,336 bytes in size.

BACKGROUND

1. Field

The present disclosure provides a stapled antimicrobial peptide (sAMP1) and particularly, a stapled antimicrobial peptide (sAMP1) that can be used as a microbial inhibitor.

2. Description of the Related Art

Bacterial infection remains a significant threat to human life due to its increasing resistance to conventional antibiotics, which is a growing public health concern. As a result, there is a critical need to create new antimicrobial agents with potent anti-drug-resistant microorganism activity.

One effective strategy for dealing with multidrug resistance among harmful bacteria is the production of alternative new antibacterial drugs. The remarkable antibacterial effects of antimicrobial peptides (AMPs) have been well documented. However, AMPs have yet to be developed into safe and effective treatments.

Accordingly, there remains a need for new and effective antimicrobial peptides (AMPs). Thus, new stapled antimicrobial peptides as antimicrobial agents solving the aforementioned problems are desired.

SUMMARY

The present subject matter pertains to a stapled antimicrobial peptide (sAMP1), and its use as an antimicrobial agent and an inhibitor of cancer cell growth.

In an embodiment, the present subject matter relates to a stapled antimicrobial peptide (sAMP1) having the sequence FFRKSKEK-S5-GKE-S5-KRIV (SEQ ID NO: 1). The sAMP1 includes alpha-4-n-pentenylalanine (S5) residues (non-naturally occurring amino acid residues) and a $C_{10}$ hydrocarbon staple stapled to the two S5 residues. In an embodiment, the present subject matter relates to a pharmaceutical composition comprising the sAMP1 peptide and a pharmaceutically acceptable carrier.

In an embodiment, the present subject matter relates to a process for the synthesis of the sAMP1 peptide, including providing a cathelicidin antimicrobial peptide having the sequence FFRKSKEKIGKEFKRIV (SEQ ID NO: 2), and replacing the isoleucine at position 9 of SEQ ID NO: 2 and the phenylalanine residue at position 13 of SEQ ID NO: 2 with alpha-4-n-pentenylalanine residues (S5).

Further contemplated herein are pharmaceutical compositions comprising the stapled antimicrobial peptide (sAMP1) of SEQ ID NO: 1, as well as methods for inhibiting microbial growth or treating or ameliorating microbial infections or cancer by administering the stapled antimicrobial peptide (sAMP1) of SEQ ID NO: 1 to a patient in need thereof.

These and other features of the present subject matter will become readily apparent upon further review of the following specification.

DETAILED DESCRIPTION OF THE PREFERRED EMBODIMENTS

Figure 1A:
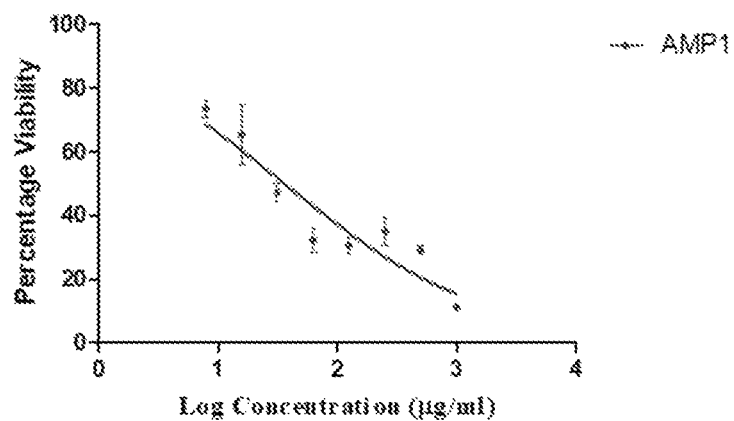
FIG. 1A depicts a graph of the cytotoxicity of sAMP1 (SEQ ID NO: 1) when incubated over 24 hours with MCF-7 cells.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer or a bacterial infection.

"Hydrocarbon staple" refers to a hydrocarbon chain that may be chemically bonded at each end of the chain to a different amino acid residue, effectively "stapling" or connecting the hydrocarbon chain to the amino acid sequence.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter pertains to the field of pharmaceuticals, particularly to a stapled antimicrobial peptide (sAMP1) (SEQ ID NO: 1) and its use as an antimicrobial agent.

In an embodiment, the present subject matter relates to a stapled antimicrobial peptide (sAMP1) having the sequence FFRKSKEK-S5-GKE-S5-KRIV (SEQ ID NO: 1). The sAMP1 (SEQ ID NO: 1) includes the non-naturally occurring amino acid alpha-4-n-pentenylalanine (S5) residues and a $C_{10}$ hydrocarbon staple stapled to the two S5 residues. In an embodiment, the present subject matter relates to a composition comprising the sAMP1 peptide (SEQ ID NO: 1) and a pharmaceutically acceptable carrier.

In an embodiment, the present subject matter relates to a process for the synthesis of a sAMP1 peptide including providing a cathelicidin antimicrobial peptide having the sequence FFRKSKEKIGKEFKRIV (SEQ ID NO: 2), replacing two amino acid residues of SEQ ID NO: 2 with non-naturally occurring amino acid residues, stapling a hydrocarbon staple to the non-naturally occurring amino acid residues employing the i, i+4 stapling approach, performing ring-closure metathesis using Grubbs reaction, and using hydrochloride salt as a counter ion.

In an embodiment, the present subject matter relates to a process for the synthesis of the sAMP1 peptide (SEQ ID NO: 1), including providing a cathelicidin antimicrobial peptide having the sequence FFRKSKEKIGKEFKRIV (SEQ ID NO: 2), replacing the isoleucine at position 9 of SEQ ID NO: 2 and the phenylalanine residue at position 13 of SEQ ID NO: 2 with alpha-4-n-pentenylalanine residues (S5); and bonding a hydrocarbon chain to the alpha-4-n-pentenylalanine (S5) residues. In an embodiment, the hydrocarbon chain bonded to the alpha-4-n-pentenylalanine (S5) residues can include a $C_{10}$ hydrocarbon staple. In an embodiment, the method can include performing ring-closure metathesis using Grubbs reaction. In an embodiment, a hydrochloride salt can be used as a counter ion.

Further contemplated herein are pharmaceutical compositions comprising the stapled antimicrobial peptide (sAMP1) (SEQ ID NO: 1), as well as methods of inhibiting microbial growth or treating or ameliorating microbial infections or cancer by administering the stapled antimicrobial peptide (sAMP1) (SEQ ID NO: 1) to a patient in need thereof.

In one embodiment, the microbial infection may be caused by *Staphylococcus aureus* or MRSA.

In an embodiment, the hydrocarbon staple may have the following chemical structure:

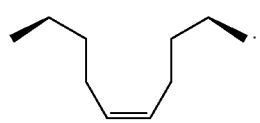

In one embodiment, the cancer may be breast cancer or lung cancer.

In one embodiment, the sAMP1 peptide (SEQ ID NO: 1) may have a molecular weight of 2,129.7 Daltons.

In one embodiment, the sAMP1 (SEQ ID NO: 1) may be amidated at the C-terminus, i.e. a —$NH_2$ group may be added to the carboxylic acid of the valine[17] residue. This amidation may increase the positive charge of the sAMP1 peptide.

In one embodiment, the present stapled peptides can be made according to the general methods taught in Phillips, C., et al. ("Design and Structure of Stapled Peptides Binding to Estrogen Receptors", J. Am. Chem. Soc. 2011, 133 (25): pp. 9696-9).

In another embodiment, the present subject matter is directed to pharmaceutical compositions comprising a therapeutically effective amount of the sAMP1 peptide (SEQ ID NO: 1) as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition comprising the sAMP1 peptide (SEQ ID NO: 1) together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present peptides are typically administered at a therapeutically or pharmaceutically effective dosage, e.g., a dosage sufficient to provide treatment for a bacterial infection. Administration of the peptide or pharmaceutical compositions thereof can be by any method that delivers the compounds systemically and/or locally. These methods include oral routes, parenteral routes, intraduodenal routes, and the like.

While human dosage levels have yet to be optimized for the present peptide, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the peptide of SEQ ID NO: 1 for treatment of a bacterial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present peptide can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present peptide may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of sAMP1 (SEQ ID NO: 1), the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the sAMP1 peptide may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the stapled antimicrobial peptide (sAMP1) (SEQ ID NO: 1) for the treatment of microbial infections, such as *Staphylococcus aureus* or methicillin-resistant *Staphylococcus aureus* (MRSA). For example, the stapled antimicrobial peptide (sAMP1) (SEQ ID NO: 1) can be used to inhibit a bacterial infection in a patient. In an embodiment, the stapled antimicrobial peptide (sAMP1) (SEQ ID NO: 1) can be used to treat cancer in a patient.

In an embodiment, the stapled antimicrobial peptide (sAMP1) (SEQ ID NO: 1) can be used to inhibit a bacterial infection in a patient. In this regard, the present compounds can exhibit a MIC of about 16.67 µg/ml against both *Staphylococcus aureus* and MRSA.

The present subject matter further relates to a method of treating or preventing a disease comprising administering to a patient in need thereof a therapeutically effective amount of the stapled antimicrobial peptide (sAMP1) (SEQ ID NO: 1).

In particular, the present subject matter relates to a method of treating one of the above-mentioned diseases or disorders comprising administering to a patient in need thereof a therapeutically effective amount of the stapled antimicrobial peptide (sAMP1) (SEQ ID NO: 1).

In the above methods, the patient is preferably a mammal, more preferably a human. Furthermore, in the above methods, the sAMP1 peptide (SEQ ID NO: 1) can be used in combination therapy with one or more additional active agents.

The following examples relate to various methods of manufacturing certain specific compounds as described herein. All compound numbers expressed herein are with reference to the synthetic pathway figures shown above.

Examples

Solid-Phase Peptide Synthesis

Fmoc-based solid peptide synthesis was used to synthesize sAMP1 peptide (SEQ ID NO: 1). The stapling technique used in synthesizing hydrocarbon-staple antimicrobial peptide (sAMP1) (SEQ ID NO: 1) was the established technique published by Phillips, C. et al. sAMP1 (SEQ ID NO: 1) was synthesized via an i, i+4 stapling approach in which two non-natural amino acids were incorporated in the original sequence of a cathelicidin antimicrobial peptide having the sequence FFRKSKEKIGKEFKRIV (SEQ ID NO: 2). The non-natural amino acids were alpha-4-n-pentenylalanine (S5) residues and both S5 residues replaced the isoleucine and phenylalanine residues at position 9 and 13 in the original sequence (SEQ ID NO: 2). The ring-closure metathesis was done using Grubbs reaction. The sAMP1 peptide counter ion was hydrochloride (HCl) salt. RP-HPLC was used to confirm the purity of sAMP1 and mass spectroscopy confirmed that sAMP1 has a molecular weight of 2129.7 Daltons.

sAMP1 was amidated at the C-terminus i.e., —$NH_2$ group was added to the carboxylic acid of the valine[17] residue. The amidation increased the positive charge of the sAMP1 peptide.

Screening of Synthesized AMPs for Antimicrobial Analysis

The agar diffusion method was used to examine the synthesized AMP's antibacterial activity. Pure colonies of *Staphylococcus aureus* and MRSA were used for antibacterial susceptibility testing according to Clinical Laboratory Standards Institute (CLSI) 2021 guideline by using a modified Kirby-Bauer disk diffusion technique (Humphries, R. et al, "Overview of Changes to the Clinical and Laboratory Standards Institute Performance Standards for Antimicrobial Susceptibility Testing", M100, 31$^{st}$ Edition, J. Clin. Microbiol. 2021 Nov. 18; 59 (12): e0021321). In brief, homogeneous colonies were chosen from each microbial strain and grown on Mullar Hilton broth at log phase. 0.5 McFarland standard culture was used to spread on to the Mullar Hilton agar plates. Freshly prepared (30 µl each) of Kanamycin 50 µg/ml and sAMP1 100 µg/ml was poured into 4 mm diameter well, blank well with an equivalent amount of saline served as a positive control. The plates were incubated for 24 hours, and the diameter of the inhibition zone was measured to determine susceptibility or resistance. The full analysis was carried out three times.

Determination of Minimum Inhibitory Concentration (MIC)

The resazurin-based turbidometric (TB) assay was adopted to demonstrate the inhibition effects of AMPs against *S. aureus* and MRSA. The standard antibiotic kanamycin was used as a positive control. Broth microdilutions were performed precisely according to the Clinical and Laboratory Standards Institute (CLSI) protocol.

In a 96-well round-bottom microtiter plate, for each bacteria culture, the assay was conducted in triplicate with positive control kanamycin and negative control as no inoculum. In the first well, 200 µL of 2×LB media was mixed with 100 µg/ml sAMP1 and then 2-fold serially diluted. Lastly, 100 µl was removed from the eighth well and discarded. The final concentration of antibiotics and sAMP1 was now one-half of the original concentration in each well. Similarly, kanamycin was added in a range of 10 µg/ml to 0.15625 µg/ml.

Then, 5 µl of diluted bacterial suspension ($1.5 \times 10^6$ cell/ml) was added into all wells except the negative control wells and mixed thoroughly. Microdilution was performed in triplicate for each bacterial species. After an overnight incubation at 37° C., growth was observed and recorded. The lowest concentration prior to color change was considered as the Minimum Inhibitory Concentration (MIC).

Cytotoxicity & MTT Testing

Cell line MCF-7 and A549 cells were cultured under $CO_2$ (5%) at 37° C. using Dulbecco's Modified Eagle's Medium (DMEM), accompanied with 1% mixture of "Penicillin-Streptomycin", 10% Fetal Bovine Serum (FBS) and 1% L-Glutamine.

Results

The agar diffusion method was used to test antimicrobial susceptibility, and the results are summarized in Table 1. Antimicrobial assessment showed potent activity against the *S. aureus* and MRSA with ZOI (22.52±2.15 and 25.31±1.53).

TABLE 1

Zone of inhibition obtained during agar diffusion test by sAMP1 as compared to Kanamycin

| Bacteria | Zone of Inhibition (mm), Mean ± SD, n = 3 | |
| --- | --- | --- |
| | SAMP1 | Kanamycin |
| *Staphylococcus aureus* | 22.52 ± 2.15 | 19.14 ± 1.38 |
| MRSA | 25.31 ± 1.53 | 21.62 ± 2.17 |

Minimum inhibitory concentration (MIC) was obtained from the agar diffusion test, comparing sAMP1 to kanamycin. The results are presented in Tables 2 and 3.

TABLE 2

MIC obtained during agar diffusion text by sAMP1 as compared to Kanamycin. Results presented as mean ± SD, n = 3.

| Microorganism | MIC (µg/ml) SAMP1 | MIC (µg/ml) Kanamycin |
| --- | --- | --- |
| *Staphylococcus aureus* | 16.67 | 3.125 |
| MRSA | 16.67 | 3.125 |

TABLE 3

MIC 96-well agar plate results

| | Kanamycin μg/ml | sAMP1 μg/ml | MRSA-sAMP1 | | | MRSA-Kanamycin | | |
|---|---|---|---|---|---|---|---|---|
| | | | 1 | 2 | 3 | 1 | 2 | 3 |
| A | 10 | 100 | x | x | x | x | x | x |
| B | 5 | 50 | x | x | x | x | x | x |
| C | 2.5 | 25 | x | x | x | x | x | x |
| D | 1.25 | 12.5 | x | Growth | x | x | Growth | x |
| E | 0.625 | 6.25 | Growth | Growth | Growth | Growth | Growth | Growth |
| F | 0.3125 | 3.125 | Growth | Growth | Growth | Growth | Growth | Growth |
| G | 0.15625 | 1.5625 | Growth | Growth | Growth | Growth | Growth | Growth |
| H | Control | Control | Control | Control | Control | Control | Control | Control |

Figure 1B:
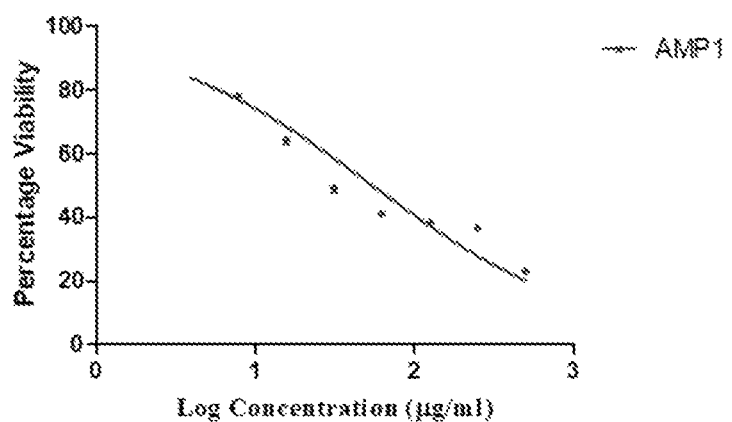
FIG. 1B depicts a graph of the cytotoxicity of sAMP1 (SEQ ID NO: 1) when incubated over 24 hours with A549 cells.

The percentage cell viabilities of MCF-7 breast cancer cells and A549 lung cancer cells against varying concentrations of sAMP1 (SEQ ID NO: 1) are depicted in FIGS. 1A-1B. The effect of sAMP1 (SEQ ID NO: 1) on cell proliferation was examined at 7.81-1000 μg/mL, where the observed $IC_{50}$ values were 35.82 and 54.22 μg/mL at 24 h against MCF-7 and A549 cells, respectively. The MTT assay results demonstrate a dose-dependent anti-cell proliferation of AMP1 against MCF-7 and A549.

One important consideration for determining if medication candidates will work in a medical context is cytotoxicity. As such, using MCF-7 and A549 tumor cells as test subjects, the cytotoxicity of the sAMP1 was evaluated. Intriguingly, at a concentration of 25 μg/ml, sAMP1 (SEQ ID NO: 1) significantly reduced the proliferation of MCF-7 and A549 cells while only mildly harming tumor cells. sAMP1 is a possible option for an anticancer medication due to its great selectivity to tumor cells. Completely overcoming AMP toxicity while maintaining a potent antibacterial action are challenging tasks. The design of AMPs must therefore strike a compromise between great efficacy and minimal toxicity. Peptides are excellent building blocks for the creation of brand-new antibacterial and antibiofilm reagents.

It is to be understood that the stapled antimicrobial peptide is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

---

We claim:

1. A stapled antimicrobial peptide consisting of the sequence FFRKSKEK-S5-GKE-S5-KRIV (SEQ ID NO: 1), wherein each S5 residue is alpha-4-n-pentenylalanine, and wherein the S5 residues combined form a $C_{10}$ hydrocarbon staple.

2. The stapled antimicrobial peptide of claim 1, wherein the C-terminal valine is amidated.

3. A pharmaceutical composition comprising the stapled antimicrobial peptide of claim 1 and a pharmaceutically acceptable carrier.

4. A method of inhibiting bacterial growth of *Staphylococcus aureus*, comprising administering the pharmaceutical composition of claim 3 to a subject in need thereof.

5. The method of claim 4, wherein the bacterial growth comprises growth of methicillin-resistant *Staphylococcus aureus*.

6. A method of inhibiting the growth of breast or lung cancer cells, comprising administering the pharmaceutical composition of claim 3 to a subject in need thereof.

* * * * *

SEQUENCE LISTING

```
Sequence total quantity: 2
SEQ ID NO: 1           moltype = AA  length = 17
FEATURE                Location/Qualifiers
source                 1..17
                       mol_type = protein
                       organism = synthetic construct
MOD_RES                9
                       note = alpha-4-n-pentenylalanine
MOD_RES                13
                       note = alpha-4-n-pentenylalanine
BINDING                9..13
                       note = hydrocarbon staple
SEQUENCE: 1
FFRKSKEKXG KEXKRIV                                                   17

SEQ ID NO: 2           moltype = AA  length = 17
FEATURE                Location/Qualifiers
source                 1..17
                       mol_type = protein
                       organism = synthetic construct
SEQUENCE: 2
FFRKSKEKIG KEFKRIV                                                   17
```